(12) United States Patent
Rivelli, Jr. et al.

(10) Patent No.: US 7,294,137 B2
(45) Date of Patent: Nov. 13, 2007

(54) DEVICE FOR MULTI-MODAL TREATMENT OF VASCULAR LESIONS

(75) Inventors: Patrick Rivelli, Jr., Palo Alto, CA (US); Alec Piplani, San Jose, CA (US); Sean Donahue, El Granada, CA (US); Arani Bose, Pelham, NY (US); Alexander Leynov, Walnut Creek, CA (US)

(73) Assignee: Boston Scientific Scimed, Maple Grove, MN (US)

( * ) Notice: Subject to any disclaimer, the term of this patent is extended or adjusted under 35 U.S.C. 154(b) by 731 days.

(21) Appl. No.: 10/109,112

(22) Filed: Mar. 27, 2002

(65) Prior Publication Data

US 2002/0161342 A1    Oct. 31, 2002

Related U.S. Application Data

(60) Provisional application No. 60/279,172, filed on Mar. 27, 2001.

(51) Int. Cl.
*A61M 29/00*    (2006.01)

(52) U.S. Cl. ...................... 606/191; 128/898

(58) Field of Classification Search ............. 606/108, 606/114, 127, 194, 200, 214; 604/273; 600/433, 600/434, 435, 585; 424/422, 423
See application file for complete search history.

(56) References Cited

U.S. PATENT DOCUMENTS

| | | | |
|---|---|---|---|
| 3,868,956 A * | 3/1975 | Alfidi et al. ............... 606/194 |
| 4,494,531 A | 1/1985 | Gianturco | |
| 4,503,569 A | 3/1985 | Dotter | |
| 4,512,338 A * | 4/1985 | Balko et al. ............... 606/108 |
| 4,820,298 A | 4/1989 | Leveen et al. | |
| 4,923,464 A | 5/1990 | DiPisa, Jr. | |
| 4,994,069 A | 2/1991 | Ritchart et al. | |
| 5,108,407 A | 4/1992 | Geremia et al. | |
| 5,122,136 A | 6/1992 | Guglielmi et al. | |
| 5,203,777 A * | 4/1993 | Lee ......................... 604/529 |
| 5,217,484 A | 6/1993 | Marks | |
| 5,234,437 A * | 8/1993 | Sepetka ..................... 606/108 |
| 5,250,071 A | 10/1993 | Palermo | |
| 5,261,916 A | 11/1993 | Engelson | |
| 5,304,195 A | 4/1994 | Twyford et al. | |
| 5,350,397 A | 9/1994 | Palermo et al. | |
| 5,354,295 A | 10/1994 | Guglielmi et al. | |
| 5,423,829 A | 6/1995 | Pham et al. | |
| 5,624,449 A | 4/1997 | Pham et al. | |
| 5,667,767 A | 9/1997 | Greff et al. | |
| 5,669,905 A | 9/1997 | Scheldrup et al. | |
| 5,690,671 A | 11/1997 | McGurk et al. | |
| 5,695,480 A | 12/1997 | Evans et al. | |
| 5,702,361 A | 12/1997 | Evans et al. | |
| 5,830,178 A | 11/1998 | Jones et al. | |
| 5,851,508 A | 12/1998 | Greff et al. | |
| 5,855,578 A | 1/1999 | Guglielmi et al. | |
| 5,879,361 A * | 3/1999 | Nash ......................... 606/159 |
| 5,891,128 A | 4/1999 | Gia et al. | |
| 5,891,130 A | 4/1999 | Palermo et al. | |
| 5,895,385 A | 4/1999 | Guglielmi et al. | |
| 5,925,037 A | 7/1999 | Guglielmi et al. | |
| 5,925,062 A | 7/1999 | Purdy | |
| 5,928,226 A | 7/1999 | Guglielmi et al. | |
| 5,935,148 A | 8/1999 | Villar et al. | |
| 5,941,888 A | 8/1999 | Wallace et al. | |
| 5,944,714 A | 8/1999 | Guglielmi et al. | |
| 5,947,962 A | 9/1999 | Guglielmi et al. | |
| 5,947,963 A | 9/1999 | Guglielmi | |
| 5,964,797 A | 10/1999 | Ho | |
| 5,976,126 A | 11/1999 | Guglielmi | |
| 5,984,929 A | 11/1999 | Bashiri et al. | |
| 6,010,498 A | 1/2000 | Guglielmi | |
| 6,017,977 A | 1/2000 | Evans et al. | |
| 6,063,070 A | 5/2000 | Eder | |
| 6,063,104 A | 5/2000 | Villar et al. | |
| 6,066,133 A | 5/2000 | Guglielmi et al. | |
| 6,077,260 A | 6/2000 | Wheelock et al. | |
| 6,083,220 A | 7/2000 | Guglielmi et al. | |
| 6,086,577 A | 7/2000 | Ken et al. | |
| 6,146,373 A | 11/2000 | Cragg et al. | |
| 6,156,061 A | 12/2000 | Wallace et al. | |
| 6,165,178 A | 12/2000 | Bashiri et al. | |
| 6,193,708 B1 | 2/2001 | Ken et al. | |
| 6,281,263 B1 | 8/2001 | Evans et al. | |
| 6,303,100 B1 | 10/2001 | Ricci et al. | |
| 6,335,384 B1 | 1/2002 | Evans et al. | |
| 6,342,202 B1 | 1/2002 | Evans et al. | |
| 6,344,041 B1 | 2/2002 | Kupiecki et al. | |

* cited by examiner

*Primary Examiner*—Michael J. Hayes
*Assistant Examiner*—Victor Nguyen
(74) *Attorney, Agent, or Firm*—Vista IP Law Group LLP

(57) ABSTRACT

A device and method for permitting multi-modal treatment of vascular lesions are disclosed. The device includes an outer delivery catheter, an inner delivery catheter, and a guidewire. The catheter is designed to pass through the inner lumen of the outer delivery catheter, and the guidewire is designed to pass through the inner lumen of the inner delivery catheter. A stent may be loaded inside the outer delivery catheter, with the distal tip of the inner delivery catheter abutting against the proximal end of the self-expanding stent, for pushing the stent distally through the outer delivery catheter.

6 Claims, No Drawings

DEVICE FOR MULTI-MODAL TREATMENT OF VASCULAR LESIONS

This application claims priority to U.S. Provisional Application Ser. No. 60/279,172 filed Mar. 27, 2001, which is incorporated in its entirety herein by reference.

BACKGROUND OF THE INVENTION

Rupture of non-occlusive cerebrovascular lesions, such as intracranial saccular aneurysms, arterio-venous malformations, and arterio-venous fistulae, is a major cause of stroke. Rupture of a lesion causes subarachnoid hemorrhage in which blood from a ruptured vessel spreads over the surface of the brain. About 2.5% of the United States population (4 million Americans) have an unruptured lesion. About 100,000 of these people suffer a subarachnoid hemorrhage each year. The disease is devastating, often affecting healthy people in their 40's and 50's, with half of the rupture victims succumbing within a month, and with half the survivors becoming seriously disabled as a result of the initial hemorrhage or of a delayed complication.

Neurovascular arteries are generally quite small, having a diameter ranging from 2.0 to 4.0 mm in the Circle of Willis, 2.5 to 5.5 mm in the cavernous segment of the internal carotid artery, 1.5 to 3.0 mm in the vessels of the distal anterior circulation, and 2.0 to 4.0 mm in the posterior circulation. The incidence of non-occlusive cerebrovascular lesions varies with the location, with 50% occurring in the Circle of Willis, 30% in the internal carotid, 15% in the distal anterior circulation, and 5% in the posterior circulation.

Screening for these lesions and preventing rupture will lead to better clinical outcomes and lower costs. Non-invasive treatments for ruptured and unruptured lesions are preferred over surgical interventions due to lower costs, lower mortality and morbidity, and patient preference.

An increasing number of non-invasive treatments are multi-modal, i.e. they utilize two or more different treatments to cure a single lesion. For example, many aneurysms are treated by implanting a stent across the neck of the aneurysm, then filling the aneurysm sac with detachable metallic coils (such as Guglielmi Detachable Coils (Boston Scientific/Target of Fremont, Calif.)) or with a liquid embolic (such as Onyx (Micro Therapeutics, Inc. of San Clemente, Calif.)). Arterio-venous malformations may be treated using a combination of pushable coils, such as those available from Cook Corporation of Bloomington, Indiana, and glue, such as NBCA available from Cordis Neuro Vascular of Miami Lakes, Fla.

However, prior art delivery systems are suitable for only a single treatment modality. As a result, multi-modal treatments require the physicians to utilize several delivery systems. Each time a new delivery system is required, the physician must remove the old delivery system, insert the new delivery system, and re-access the lesion. These extra steps increase the time and the risk of the procedure. It is also possible that it will be impossible to re-access the lesion, resulting in a treatment failure.

It would therefore be valuable to provide a delivery system that permits multi-modal treatment to be performed using a single delivery device.

SUMMARY OF THE INVENTION

The invention, in one aspect, includes three elements:
An outer catheter;
An inner catheter, designed such that the outer diameter of this catheter is slightly smaller than the inner diameter of the outer catheter, so that the inner catheter may pass through the outer catheter;
A guidewire, capable of passing through the I.D. of the inner catheter.

In one embodiment, the outer catheter is a 3 French O.D. microcatheter, which may be a variable-stiffness microcatheter; may be braided; may have a lubricious inner liner; and may be coated on the O.D. with a hydrophilic or other lubricious coating. The outer catheter is capable of accessing lesions through tortuous anatomy, such as lesions deep in the intracranial circulation. The outer catheter may have an I.D. of approximately 2.1 French.

In this embodiment, the inner catheter has an O.D. of 2 French, allowing it to fit inside the outer catheter. The inner catheter has an I.D. of approximately 0.016". The inner catheter may have two platinum tip markers, spaced to permit deployment of electrolytically detachable coils (such as Guglielmi Detachable Coils). The inner catheter may be composed of materials that are compatible with liquid embolics, including DMSO-based embolics (such as Onyx).

In this embodiment, the guidewire has an O.D. of approximately 0.014".

In another embodiment, a self-expanding stent is loaded into the distal end of the outer catheter. The stent can be compressed and placed into the I.D. of the catheter, such that stent can be advanced proximally and distally through the I.D. of the catheter. The inner catheter is designed such that the distal tip of the inner catheter butts against the proximal end of the stent. The inner catheter is capable of pushing the stent distally, out of the outer catheter, in order to deploy the stent.

In yet another embodiment, the outer catheter is designed to permit pushable coils to be introduced into the catheter hub and be pushed through the catheter I.D. (such as 0.025" pushable coils).

The inner catheter is designed such that the distal tip of the inner catheter butts against the pushable coil. The inner catheter is capable of pushing the pushable coil distally, through the outer catheter, in order to deliver the coil.

In addition, the inner catheter also permits pushable coils (such as 0.010" pushable coils) to be introduced into the catheter hub and pushed through the catheter I.D. A standard coil pusher (such as an 0.014" coil pusher) is capable of pushing the pushable coil distally, through the inner catheter, in order to deliver the coil.

The invention claimed is:

1. A method of performing a multi-modal treatment of a non-occlusive cerebrovascular lesion comprising:
   providing a delivery system comprising:
   an outer delivery catheter:
   an inner delivery catheter, and
   a guidewire, wherein
      the inner delivery catheter is designed to pass through the inner lumen of the outer delivery catheter, and
   the guidewire is designed to pass through the inner lumen of the inner delivery catheter, and wherein
      the outer delivery catheter has an O.D. of about 3 French and an I.D. of about 2 French, the inner delivery catheter has an O.D. of about 2.1 French and an I.D. of 0.016" and the guidewire has an O.D. of 0.014" the inner delivery catheter and the guidewire are each dimensioned to permit multi-modal treatment of the non-occlusive cerebrovascular lesion,
   positioning said delivery system in a cerebrovascular blood vessel proximate to a lesion,
   utilizing said delivery system to perform at least two of the procedures selected from the group consisting of (i) deploying an occlusive coil to the lesion, (ii) deploying a liquid embolic material to the lesion, (iii) deploying an acrylic glue to the lesion, and (iv) deploying a self-expanding stent to the lesion.

2. The method of claim 1, where the inner delivery catheter has two radiopaque markers near its distal tip, spaced to be compatible with deployment of an electrolytically detachable coil.

3. The method of claim 1, where the inner delivery catheter is compatible with liquid.

4. The method of claim 1, where the inner delivery. catheter is compatible with acrylic glues.

5. The method of claim 1, where the inner delivery catheter is capable of pushing the coil from the hub of the outer catheter, through the outer catheter, and through the distal tip of the outer catheter to deliver the coil to the intracranial lesion, the coil remaining at the cerebrovascutar lesion when the delivery system is removed.

6. The delivery system method of claim 1, where the guidewire is adapted to push the coil from the hub of the inner catheter, through the inner catheter, and through the distal tip of the inner catheter to deliver the coil to the non-occlusive cerebrovascular lesion, the coil remaining at the cerebrovascular lesion when the delivery system is removed.

* * * * *